(12) United States Patent  
Müller

(10) Patent No.: US 8,297,112 B2  
(45) Date of Patent: Oct. 30, 2012

(54) DEVICE FOR DETERMINING AND/OR MONITORING A PROCESS VARIABLE OF A MEDIUM

(75) Inventor: Alexander Müller, Sasbach-Jechtingen (DE)

(73) Assignee: Endress + Hauser GmbH+Co. KG, Maulburg (DE)

( * ) Notice: Subject to any disclaimer, the term of this patent is extended or adjusted under 35 U.S.C. 154(b) by 930 days.

(21) Appl. No.: 11/887,743

(22) PCT Filed: Mar. 15, 2006

(86) PCT No.: PCT/EP2006/060742  
§ 371 (c)(1),  
(2), (4) Date: Jan. 13, 2009

(87) PCT Pub. No.: WO2006/106028  
PCT Pub. Date: Oct. 12, 2006

(65) Prior Publication Data  
US 2009/0205411 A1    Aug. 20, 2009

(30) Foreign Application Priority Data  
Apr. 4, 2005   (DE) .......................... 10 2005 015 547

(51) Int. Cl.  
*G01N 29/00*    (2006.01)

(52) U.S. Cl. ........................................ 73/64.53

(58) Field of Classification Search ................ 73/64.53, 73/290 V  
See application file for complete search history.

(56) References Cited

U.S. PATENT DOCUMENTS

| | | | | |
|---|---|---|---|---|
| 5,237,288 A * | 8/1993 | Cleveland | ...................... | 330/107 |
| 5,844,491 A | 12/1998 | Getman | ........................ | 340/612 |
| 6,138,507 A * | 10/2000 | Getman et al. | ............... | 73/290 V |
| 6,236,322 B1 * | 5/2001 | Lopatin et al. | ................. | 340/612 |
| 2004/0078164 A1 | 4/2004 | Lopatin | .......................... | 702/100 |

FOREIGN PATENT DOCUMENTS

| DE | 102 37 931 A1 | 2/2004 |
|---|---|---|
| EP | 0 209 872 A | 1/1987 |
| WO | WO 2004/018974 A2 | 3/2004 |

* cited by examiner

*Primary Examiner* — Peter Macchiarolo  
*Assistant Examiner* — Tamiko Bellamy  
(74) *Attorney, Agent, or Firm* — Bacon & Thomas, PLLC

(57) ABSTRACT

An apparatus for determining and/or monitoring at least one process variable of a medium. The apparatus includes: at least one mechanically oscillatable unit; a driving/receiving unit, which, starting with an electric, excitation signal, excites the mechanically oscillatable unit to execute mechanical oscillations, and which receives the mechanical oscillations of the mechanically oscillatable unit and converts them into an electric, received signal; and an electronics unit, which, starting with the electric, received signal, generates the electric, excitation signal and sends it to the driving/receiving unit. The electronics unit is embodied in such a way that it generates the excitation signal, such that a predeterminable phase difference exists between the excitation signal and the received signal. Present in the electronics unit is at least one all-pass filter for tuning the phase difference.

8 Claims, 3 Drawing Sheets

DEVICE FOR DETERMINING AND/OR MONITORING A PROCESS VARIABLE OF A MEDIUM

TECHNICAL FIELD

The invention relates to an apparatus for determining and/or monitoring at least one process variable of a medium. The apparatus includes: at least one mechanically oscillatable unit; a driving/receiving unit, which, on the basis of an electric, excitation signal (Se), excites the mechanically oscillatable unit to execute mechanical oscillations, and which receives the mechanical oscillations of the mechanically oscillatable unit and converts such into an electric, received signal (Sr); and an electronics unit, which, on the basis of the electric, received signal (Sr), produces the electric, excitation signal (Se) and transfers it to the driving/receiving unit; wherein the electronics unit is formed such that the excitation signal is produced in such a way that a predeterminable phase difference exists between the excitation signal and received signal. The medium can be, for example, a liquid, or it can be, for example, a bulk good. The process variable can be, for example, fill level, density, or viscosity of the medium.

Measuring devices for determining process variables using mechanical oscillations of an oscillatable unit are already known. Such are mostly used as so-called limit-level switches. An embodiment is described, by way of example, in International Patent Application WO 2004/018974.

The mechanically oscillatable unit of such a measuring device is composed of at least one oscillating element (when there is only one element, it is a so-called single-rod device) or of two oscillating elements (in which case it is a so-called oscillation fork) mounted on a diaphragm. Production and detection of oscillations normally occurs using a piezoelectric element, which performs the transformation of the mechanical oscillation to an electric, alternating voltage and vice versa. The piezoelectric element thus forms the exciting/receiving unit of the measuring device. For excitation, the exciting/receiving unit is supplied with an excitation signal Se, usually an electric, alternating voltage. In turn, the unit generates a received signal Sr from the mechanical oscillations. From the frequency fr, amplitude, and phase of the received signal Sr relative to the excitation signal Se, for example, fill level, density, or viscosity of the medium can be deduced. If one of these variables is dependent on other process variables, for example, if viscosity is dependent on the temperature, then also additional process variables can be deduced.

Depending on the character of the medium, various phase differences between the excitation signal Se and the received signal Sr are advantageous. It has been shown that, in the case of high-viscosity media, a difference of approximately 70° is reasonable, and that detection of foam is possible through a phase of circa 120°. Because the excitation signal from an electronics unit in the measuring apparatus is generated from the received signal, it is possible to tune the phase of the excitation signal appropriately, such that the necessary phase difference results. A possibility for realizing this digitally is discussed in the above named application WO 2004/018974.

However, especially high-viscosity media are problematic in that they cause the oscillations of the oscillatable unit to experience a high damping. Therefore, it is necessary that the frequency fe of the excitation signal Se be as equal as possible to the frequency fr of the received signal Sr, because, with deviations, the oscillations can break off. It is also described in the above-named document WO 2004/018974 how the frequency can be determined digitally.

The method for fundamental-wave excitation discussed in the document WO 2004/018974 has two disadvantages, however, which complicate its usage in high-viscosity media. One difficulty—a static one, so to speak—arises in the digitizing of the frequency, in which case the precision is defined by the resolution of the microprocessor used. A deviation from the actual frequency thereby results, which can lead to a breaking off of the oscillations. Additionally, there is a problem—a dynamic one, so to speak—in that the frequency is achieved by evaluating the edges of the received signal Sr, and, if necessary, by averaging over multiple periods. In the case of high-viscosity media and a gradually changing covering of the oscillatable unit by the medium, however, the oscillation frequency can change from one half-period to another. This leads necessarily to the excitation signal Se carrying an inappropriate frequency. In principle, both problems can be overcome by increasing the computing power of the microprocessor used. However, this leads to an unreasonable cost increase of the end product.

SUMMARY OF THE INVENTION

Thus, an object of the invention is to provide a tuning of the phase difference between the excitation signal and the received signal, which tuning also permits use of the measuring device in high-viscosity media.

This object is achieved by the invention by providing in the electronics unit at least one all-pass filter for tuning the phase difference. An all-pass filter is an electronic component, which, dependent on frequency, changes the phase of an electric signal, without influencing the amplitude of the signal. Especially, an all-pass filter can be controlled, using open- or closed-loop control, in such a manner that the phase of the electric signal is adjustable. All-pass filters are, per se, well known to technically qualified personnel from the state of the art. All-pass filters are generally circuits whose amplification is constant, but which cause a frequency-dependent phase shift. In the apparatus of the invention, an all-pass filter is thus located in the electronics unit caring for the feedback. The all-pass filter tunes the phase of the excitation signal, and thus tunes the phase difference between the excitation signal and received signal.

In an embodiment, the all-pass filter is an analog all-pass filter. An analog all-pass filter has the great advantage that there can be no problems with the degree of resolution. As a result, no frequency shift can occur due to sampling. The level of precision, which, in the case of the digital embodiment can only be attained with increased costs, is automatically and implicitly given in the analog embodiment. This is an essential advantage of analog technology for the present invention. The invention thus provides that the part required for tuning the phase difference is realized through analog technology. Advantageously, the received signal Sr is only prefiltered and/or amplified, and then supplied to the all-pass filter, so that, thus, the actual received signal Sr is processed and fed back to the all-pass filter. This happens primarily using only analog components.

In an embodiment, at least one control unit is provided, which controls, using closed-loop control or open-loop control, the all-pass filter such that the phase difference between the excitation signal (Se) and the received signal (Sr) essentially corresponds to a predetermined desired value. The control unit controls the all-pass filter and tunes it according to requirements. In the case of high-viscosity media, the phase difference, for example, can be tuned to 70°, and it is tuned to 120° for detecting foam. The desired value depends on the type of application and the character of the medium. Advantageously, the control unit can be embodied digitally, in order to use the advantages of digital technology for tuning the phase; that is, to tend the analog all-pass filter digitally. For this type of control, the received signal is forwarded to the control unit, and is evaluated there at least with respect to frequency.

An embodiment provides that at least one memory unit is assigned to the control unit, in which memory unit at least one correction value for the phase difference is stored, as a function of a received frequency (fr) of the received signal (Sr). The control unit thus controls, using closed-loop or open-loop control, the all-pass filter as a function of at least one or more correction values stored in a memory unit. Advantageously, the phase-frequency curve of the all-pass filter is stored at least sectionally in the memory unit. The control unit thus references values permitting an optimal open-loop control of the all-pass filter, and thus an optimal tuning of the phase difference. If there are multiple correction values, then these can be stored, for example, in the form of a table in the memory unit. Advantageously, the frequency fr of the received signal Sr is also the excitation frequency fe of the excitation signal Se.

In an embodiment, the control unit is embodied in such a way, and is connected with the exciting/receiving unit such that, the control unit evaluates the received signal Sr at least with respect to the phase. The control unit thus determines the phase of the received signal Sr, and can, on the basis of that information, tune the all-pass filter so that the predetermined desired value for the phase difference is achieved. For determining the phase using the control unit, it is advantageous if the control unit is embodied digitally, in order to be able to determine the phase as quickly and as precisely as possible, for example, and also in order to suitably control the all-pass filter using open-loop control.

An embodiment provides that the control unit evaluates the excitation signal Se at least with respect to the phase and/or frequency. The output signal Se is directed back to the control unit, and can be used there for the open- and/or closed loop control of the all-pass filter. From the control unit, the all-pass filter is initially tuned, and the evaluation of the excitation signal generated thereby permits a more precise tuning and control of the all-pass filter. Thus, the control unit receives the received signal Sr as well as the excitation signal Se, and evaluates both signals accordingly.

In an embodiment, the control unit controls the all-pass filter, using open-loop or closed-loop control, on the basis of at least the frequency (fr) and/or phase of the received signal (Sr), and/or the frequency and/or phase of the excitation signal (Se). Thus the control unit evaluates the received signal and excitation signal in such a way that the optimal excitation signal is generated by the all-pass filter.

An embodiment provides that at least one microcontroller is provided in the control unit. Thus, the control unit itself is embodied digitally, whereas the components of the apparatus for tuning the frequency are analog. Thus the part of the apparatus which cannot negatively affect the frequency is digital. An advantage of this digital realization is that the above-named correction values can be changed more easily, and the control unit can be given an intelligence, which permits a simpler adaptation to the measuring conditions. Advantageously, the received signal (Sr) is thus amplified, i.e. fed to the all-pass filter without change of frequency, and phase is then tuned by the control unit using closed-loop or open-loop control. Therefore, as a whole, the apparatus is configured partially analogly and partially digitally.

BRIEF DESCRIPTION OF THE DRAWINGS

The invention will now be described in further detail on the basis of the drawings, the figures of which show as follows.

DETAILED DISCUSSION

Figure 1:
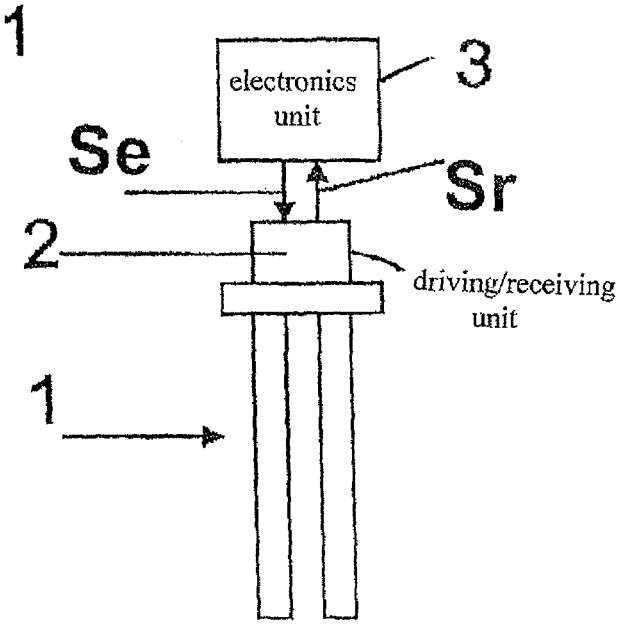
FIG. 1 a schematic illustration of the apparatus of the invention.

FIG. 1 shows the principal construction of an apparatus of the invention. In this case, the mechanically oscillatable unit 1 is an oscillatory fork composed of two oscillating elements mounted on a diaphragm. The driving/receiving unit 2 is mounted above the diaphragm and, thus, against the mechanically oscillatable unit 1. The driving/receiving unit 2 excites the mechanically oscillatable unit 1 to execute oscillations, and receives the oscillations and converts them into an electric, received signal Sr. Such is normally an electric, alternating voltage having a received frequency fr corresponding to the frequency of the oscillations of the mechanically oscillatable unit 1. The frequency fr, the amplitude, and also the phase of the received signal Sr relative to the excitation signal Se are dependent on the degree of covering of the mechanically oscillatable unit 1 by the medium (not shown), and also on the viscosity or density of the medium. The latter dependencies assume a certain degree of cover. The electronics unit 3 amplifies the received signal Sr, and supplies it back to the driving/receiving unit 2 as the excitation signal Se. The resonance circuit thus involves feedback.

Depending on the character of the medium, specific phase differences between the received signal Sr and the excitation signal Se must be set. In the case of high-viscosity media, a phase difference of circa 70° is important. The excitation frequency fe of the excitation signal Se is essentially identical to the received frequency fr of the received signal Sr, but the phase of the excitation signal is tuned such that a predetermined, desired value for the phase difference, or for the sum of all phases in the resonance circuit, is achieved, dependent on the application and the character of the medium.

Figure 2:
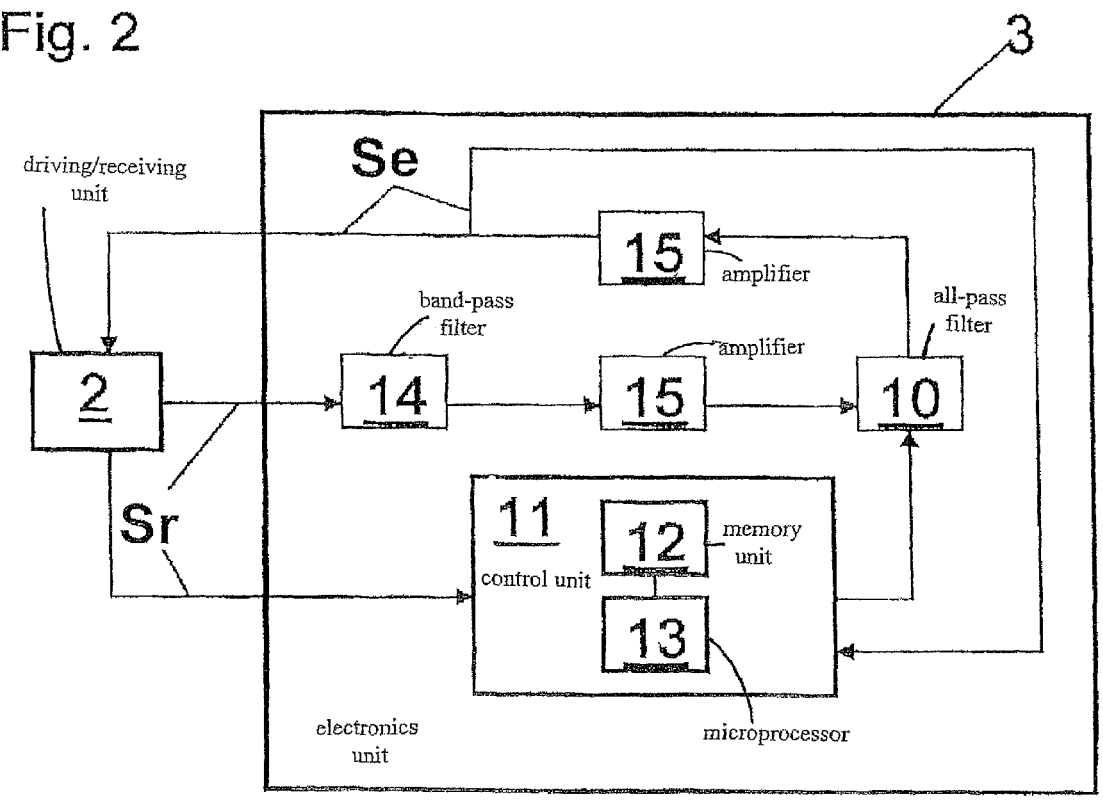
FIG. 2 a detailed illustration of the essential electronic units in the form of a block diagram.

FIG. 2 shows a block diagram of the essential electronic components of an example of an embodiment of the apparatus of the invention. In the version shown here, the exciting/receiving unit 2 forwards the received signal Sr to the electronics unit 3 on two lines. The signal Sr is forwarded directly to the band-pass filter 14, which limits noise and also lessens extraneous vibrations in the signal Sr. Next, the signal is amplified by an amplifier 15 and output to the all-pass filter 10. Phase is adjusted there, such that the desired value of phase difference is achieved. Thereafter, the signal is sent back to an amplifier 15 and leaves the electronics unit 3 then as the excitation signal Se. However, at the same time, the excitation signal Se is directed to the control unit 11. The units 14, 15, and 10 are analog, so that the frequency fe of the excitation signal Se is equal to the frequency fr of the received signal Sr. No components are used which can lead to a frequency shift, and, above all, no digital components are used, the resolution of which can influence the accuracy of agreement of the two frequencies fr and fe. All-pass filter 10 is controlled by the control unit 11 using open-loop or closed-loop control. For this, the received signal Sr is directed to the control unit 11, such that there, for example, the microprocessor 13 can determine the phase of the received signal Sr. The corresponding desired values for the phase difference between the received signal Sr and the excitation signal Se are stored in the memory unit 12. The desired values are e.g. dependent on whether media with high viscosity should be detected, or whether foam should be recognized.

Furthermore, the appropriate correction values for tuning the all-pass filter 10 are stored in memory unit 12. These are supplied to the control unit 11, so that the excitation signal Se always receives the necessary phase from the all-pass filter 10, in order that, for example, the oscillations do not break off in high-viscosity media. Through the feedback of the excitation signal Se to the control unit 11, and the evaluation there of the excitation signal Se with respect to frequency and phase, closed-loop control of the all-pass filter 10 is improved. Furthermore, it is ensured through the analog components that there is no negative influencing of frequency, and that, therefore, the excitation frequency fe is equal to the received frequency fr.

Figure 3:
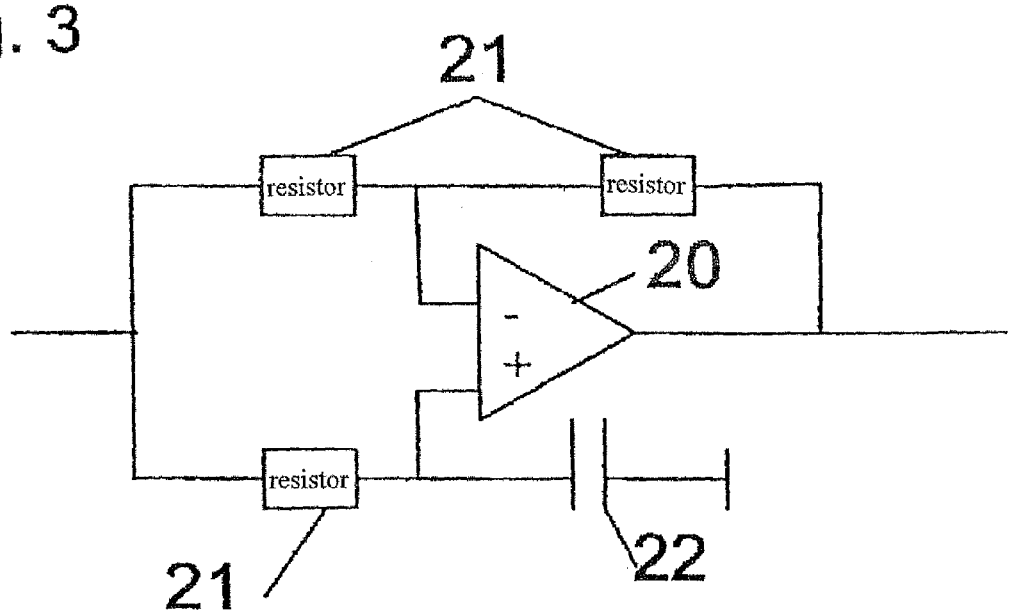
FIG. 3 an example of an embodiment of an all-pass filter.

FIG. 3 shows a concrete embodiment of an all-pass filter. It is a first-order, all-pass filter composed of an operational amplifier 20, three resistors 21, and a capacitor 22.

The invention claimed is:

1. An apparatus for determining and/or monitoring at least one process variable of a medium, comprising:
    at least one mechanically oscillatable unit;
    a driving/receiving unit, which excites said mechanically oscillatable unit to execute mechanical oscillations, starting with an electric, excitation signal, and which receives the mechanical oscillations of said mechanically oscillatable unit and converts them into an electric, received signal;
    an electronics unit, which, starting with a electric, received signal, generates the electric, excitation signal, and sends such to said driving/receiving unit, said electronics unit is provided with at least one all-pass filter for tuning the phase difference; and
    at least one control unit, which controls said all-pass filter, using closed-loop or open-loop control, such that the phase difference between the excitation signal and the received signal essentially corresponds to a predetermined, desired value, wherein:
    said electronics unit is embodied in such a manner that it generates the excitation signal such that a predeterminable phase difference exists between the excitation signal and the received signal.

2. The apparatus as claimed in claim 1, wherein:
    said all-pass filter is an analog all-pass filter.

3. The apparatus as claimed in claim 1, further comprising:
    at least one memory unit assigned to said control unit, in which memory unit at least one correction value for the phase difference is stored as a function of the received frequency of the received signal.

4. The apparatus as claimed in claim 1, wherein:
    said control unit is embodied, and connected with said exciting/receiving unit, in such a manner that said control unit evaluates the received signal at least with respect to phase.

5. The apparatus as claimed in claim 1, wherein:
    said control unit evaluates the excitation signal at least with respect to at least one of: phase and frequency.

6. Apparatus as claimed in claim 4, wherein:
    said control unit controls said all-pass filter, using closed- or open-loop control, on the basis of at least one of: frequency and phase of the received signal, and at least one of: frequency and phase of the excitation signal.

7. Apparatus as claimed in claim 1, further comprising:
    at least one microcontroller is provided in said control unit.

8. Apparatus as claimed in claim 1, wherein:
    said at least one mechanically oscillatable unit includes an oscillatory fork mounted on a diaphragm.

* * * * *